United States Patent [19]
Ross et al.

[11] Patent Number: 4,973,394
[45] Date of Patent: Nov. 27, 1990

[54] IMMOBILIZED VALINOMYCIN MOLECULE FOR K+ SENSOR

[75] Inventors: Pepi Ross, Berkeley; Allan J. Johnston, Palo Alto; Amrit K. Judd, Belmont, all of Calif.

[73] Assignee: SRI International, Menlo Park, Calif.

[21] Appl. No.: 241,110

[22] Filed: Sep. 2, 1988

[51] Int. Cl.$^5$ .......................................... G01N 27/327
[52] U.S. Cl. .................................. 204/403; 204/418; 435/4; 435/7; 435/180; 435/817; 436/528; 436/531; 436/535; 436/806
[58] Field of Search .................. 204/403, 416, 418; 435/4, 180, 181, 817, 7; 436/528, 531, 532, 535, 806

[56] References Cited

U.S. PATENT DOCUMENTS

| | | |
|---|---|---|
| 3,843,399 | 10/1974 | Kaplan et al. |
| 4,018,945 | 4/1977 | Mehalso |
| 4,020,830 | 5/1977 | Johnson et al. ............... 204/415 |
| 4,151,049 | 4/1979 | Janata |
| 4,214,968 | 7/1980 | Battaglia et al. ............... 204/418 |
| 4,476,005 | 10/1984 | Tokinaga et al. ............... 204/403 |
| 4,517,303 | 5/1985 | Freytag et al. ............... 435/4 |
| 4,608,149 | 8/1986 | Daniel et al. |
| 4,637,861 | 1/1987 | Krull et al. |

OTHER PUBLICATIONS

Gisin et al., Int. J. Peptide Protein Res. 14:356-363 (1979).
Gisin et al., J. Amer. Chem. Soc. 91:2691-2695 (1969).
Gisin et al., Biochimica et Biophysica Acta 509:201-217 (1978).
Gombotz et al., "Critical Reviews in Biocompatibility" 4(1):1-42 (1987).
Akela et al., Chem. Rev. 81(6):557-587 (1981).
Snell et al., Chem. Soc. Rev. 8(2):259-282 (1979).
Kunz, Angew Chem. Int. Ed. Engl. 17(1):67-68 (1978).
Lenhard et al., J. Amer. Chem. Soc. 100(25):7870-7875 (1978).
Afromowitz et al., J. Bioeng 1:55-60 (1976).
Kaganowicz et al., The Properties of Fluorocarbon Films Prepared by Plasma Polymerization of 1,3-Perfluorodimethylcyclohexane, 4th Instrumentation Symposium on Plasma Chemistry (1979).
Kaganowicz et al., J. Vac. Sci. Technol A 4:1901-1904 (1986).

Primary Examiner—T. Tung
Attorney, Agent, or Firm—Lisabeth Feix Murphy

[57] ABSTRACT

The present invention provides a stabilized potassium ion-selective membrane comprising lysine-substituted valinomycin covalently bound to a polymeric substrate. The membrane of the invention exhibits improved stability and is used either on ISEs or on solid-state coated wire or semiconductor devices.

22 Claims, 2 Drawing Sheets

NATIVE VALINOMYCIN

LYSINE-VALINOMYCIN

IMMOBILIZED VALINOMYCIN MOLECULE FOR K+ SENSOR

TECHNICAL FIELD

The invention relates to ion-selective membranes in which lysine-substituted valinomycin is immobilized in or on an insoluble polymeric substrate. The membranes are useful in ion-selective electrodes and solid state devices for selectively determining potassium ions in preference to other cations.

BACKGROUND OF THE INVENTION

Ion-selective electrodes (ISEs) are increasingly important tools in medicine and research. The most common example is the pH electrode which detects hydrogen ions; others include sensors for potassium, sodium, chloride, or other ions. Currently, valinomycin is the ligand with the most specificity for potassium. Potassium-sensitive membranes which can serve to isolate on internal reference electrode solution from a test solution are made by embedding or mixing valinomycin in the membrane along with several other membrane components such as a polymer matrix, solvents, and plasticizers. The difficulty with this current method is that during use, both ligand and plasticizers continuously leach out of the membrane leading to an unstable situation. This gives rise to changes in the electrical properties of the membrane and the electrode which in turn lead to electrode drift, baseline shift and the like.

Since 1972, researchers have been attempting to make an all solid state sensor based on the principles of the ISE. Attempts to eliminate the internal reference solution have generally focused on depositing the ion-selective membrane in direct contact with the internal reference electrode. Methods have varied from directly coating solid conductors—wires or planar metalized surfaces—to coating the insulator on the gate of a field effect transistor (FET).

DISCLOSURE OF THE INVENTION

The present invention provides a stabilized potassium ion-selective membrane comprising lysine-substituted valinomycin covalently bonded to an insoluble solid polymer substrate. It has been found that this membrane exhibits improved stability over those used heretofore either on ISEs or on solid-state coated wire or semiconductor devices. Further, the lifetimes of these membranes are extended because the ligand will not leach out of the membrane as currently happens. In addition, it is possible to determine the optimum concentration of ligand in the membrane and, use the present covalent bonding to produce the membrane consistently at that optimum.

Also provided in this invention is an improved potassium ion-selective sensor wherein potassium ion selectivity is imparted by the selective association of potassium ion with a valinomycin species. In this sensor the improvement comprises employing as the valinomycin species, a lysine derivative of valinomycin covalently bonded through the primary amine group of the lysine to a reactive site such as a carboxyl group present on an insoluble organic solid polymer substrate or present on a spacer which is in turn covalently bonded to the substrate. The present covalently linked valinomycins have applicability in conventional ISEs if the valinomycin molecule is immobilized to a polymer within a conductive membrane. They also find application in solid state sensors as part of a dielectrc polymer membrane coating.

MODES FOR CARRYING OUT THE INVENTION

I. Modified Valinomycin

Figure 1A:
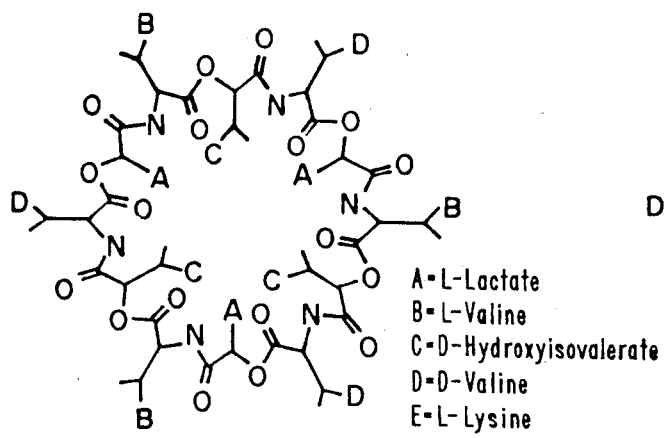
FIG. 1 is an illustration of the structure of native valinomycin (FIG. 1A) and lysine-modified valinomycin (FIG. 1B).
Figure 1B:
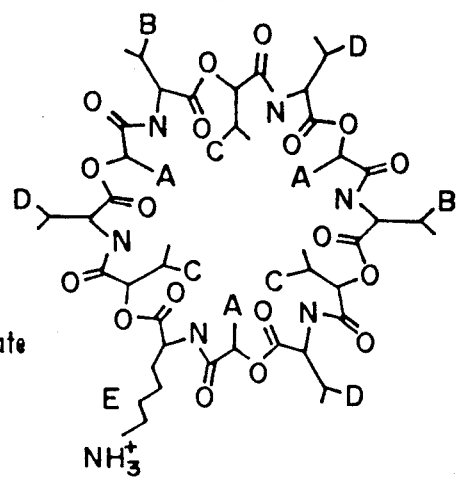

The potassium ion-selective membranes useful in the present invention include a lysine-substituted valinomycin as the ionophore, i.e., ligand. The substitution of a lysine for a valine in the valinomycin provides a side chain through which the molecule can be immobilized. The native valinomycin molecule is depicted in FIG. 1A. The exterior consists of hydrocarbon groups while the interior cavity is lined with six oxygen atoms (from the valines) which can coordinate to the potassium ion. (In water, the free potassium ion is surrounded by the oxygen atoms of water, so the transition to the oxygen atoms of valinomycin is favorable.) It is not possible to immobilize or covalently link the native valinomycin molecule through its hydrocarbon periphery without interfering with K+binding.

To prepare a valinomycin molecule that could be bound to a substrate such as a polymer membrane, valinomycin was synthesized substituting a 1-lysine for one 1-valine according to the procedure of Gisin, B. F., et al (*Int J Peptide Protein Res* 14:356–363 (1979); *J Amer Chem Soc* 91:2691–2695 (1969); *Biochimica et Biophysica Acta* 509:201–217 (1978)), the teachings of which are incorporated in their entirely herein by reference. The incorporation of a lysine provides a primary amine functionality which is a suitable attachment point. The resulting molecule binds rubidium-86 ion ($^{86}Rb^+$), a radioactive analogue of $K^+$, nearly as well as the native molecule does. Gisen et al, 1969, supra, observed decreased affinity of the modified valinomycin for $K^+$ over that of the native valinomycin when they used the molecule in a bilayer lipid membrane. Moreover, groups attached to the derivatized valinomycin molecule may distort the plane of the valinomycin and interfere with the orientation of valinomycin in the bilayer, which could be critical to binding efficiency. In the present invention, the tethering methods used do not confine the valinomycin to a bilayer so minimal reduction in binding affinity is observed.

II. Membrane Fabrication

Two embodiments of the present invention are described in detail below.! The first involves potassium-selective stabilized conducting membranes for ISE devices, and the second provides potassium-selective insulating membranes for solid state e.g. semiconducting, devices. In both cases the membranes are substantially water insoluble and generally hydrophobic, that is having a solubility in water of less than about $10^{-4}\%$ by weight.

A. Fabrication of Stabilized Conducting Membranes

The substrates used in the preparation of a conducting membrane include hydrophobic natural or synthetic polymers capable of forming thin films of sufficient permeability to produce, in combination with the valinomycin species and plasticizing agent, ionic mobility across the membrane. Conventional polymers include, without limitation, poly(vinyl chloride); poly(vinylidene chloride); poly(acrylonitrile); polyurethanes, especially aromatic polyurethanes; and copolymers of vinyl chloride and vinylidene chloride.

Conventional plasticized poly(vinyl chloride), hereinafter PVC, ion-selective membranes are generally prepared by evaporating a solution of PVC, a plasticizing agent such as dioctylsebacate and an ion carrier (valinomycin) in a common solvent such as, for example, tetrahydrofuran (THF). Valinomycin membranes prepared heretofore have a typical composition of 1 part PVC, 2 parts plasticizer, and 0.1 part valinomycin (with added lipophilic salt, K-tetraphenyl borate, to improve response). During use, both ligand and plasticizer continually migrate out of the membrane.

In the present invention, the membrane-forming polymer is selected to provide a plurality of sites for covalent attachment of the modified valinomycin. These attachment sites can be direct attachment sites for covalent bonding to the lysine primary amine itself, for example, carboxylic acid groups for direct amide coupling to the lysine-provided primary amines, or carbonyl sites for imine formation with these amines, or acid chloride sites for amide formation, or the like. They can also be sites for coupling an intermediate spacer which in turn provides covalent attachment points for the modified valinomycin. A typical substrate for forming the membrane is a carboxylated polymer such as carboxylated-PVC. Commercially available carboxylic acid-substituted PVC (PVC-COOH), consisting of 1.7% covalently bound COOH by weight of polymer, is used as the substrate for reaction with lysine-valinomycin (lys-val). The density of COOH sites on the PVC allows a wide range of lys-val loading, up to a lys-val/PVC weight ratio of greater than 25%. Once 7% of the COOH sites are derivatized, a polymer containing 3% valinomycin, as in conventional membranes, is achieved.

In addition to the commercially available carboxyl-containing PVC, one can use other active site (i.e. carboxyl, amino, and hydroxy)-containing polymers such as carboxylated poly(urethanes), and carboxylated poly(vinylidene chloride). These materials are fabricated into permeable conductor membranes by art-taught processes. The coupling of the modified valinomycin, with or without intervening spacer arms, will be set forth in section C after the description of the fabrication of the insulating membranes.

B. Fabrication and Deposition of Insulating Membranes

Glow discharge polymerization is one method useful for fabricating and depositing insoluble insulating polymer membranes on solid surfaces. The plasma polymerization of organic vapors in a radio frequency (RF) glow discharge results in highly cross-linked, chemically inert, dielectric films. Methods to achieve uniformity and stability of glow-discharge polymer depositions are disclosed in U.S. Pat. Nos. 3,843,399; 3,901,944; and 4,018,945.

The chemical, surface, and physical properties of a plasma-deposited coating are determined primarily by the type of monomer and carrier gases used in the polymer deposition procedure. The coating's properties at the substrate interface, bulk, and free surface can be independently controlled by changing the deposition parameters while the coating is being deposited. The film surface can be modified by depositing a surface layer using a hydrophobic insulating polymer such as, for example, styrene, parylene, or acetylene in the presence of oxygen, water, or nitrogen. Films prepared in the presence of oxygen and water contain molecularly bound oxygen as hydroxyl, carboxyl, and ester groups that are readily detected by infrared spectroscopy. These oxygen-containing groups can provide attachment sites for the modified valinomycin. Freshly prepared films made using argon or oxygen as carrier gas also contain free radicals that can be detected by ESR spectroscopy. Peroxides formed in the presence of oxygen can be decomposed by subsequent heating but may result in chain scission and incorporation of additional polar groups. Nitrogen, when used as a carrier gas promotes film adhesion, inhibits formation of free radical, and results in films with stable properties.

One of the embodiments of the present invention employs a plasma-polymerized film made through coating a planar metal electrode with a fluoro-monomer 1,3-perfluorodimethylcyclohexane (PFDMC), a chemical having adhesive and dielectric properties. The plasma-deposited membrane is then chemically modified such as by the method of Gomboltz, W. R., and Hoffman, A. S., in "Critical Reviews in Biocompatibility", CRC Press, Boca Raton, Fla. (1988) to introduce attachment sites such as carboxylic acid groups, hydroxyl, or carbonyl, or amino, onto the outer membrane surface. The derivatized valinomycin used in the invention is then covalently bound through its primary amino terminus either directly or through spacer arms to the attachment points, such as carboxyl groups, on the surface of the plasma-deposited film.

Figure 2:
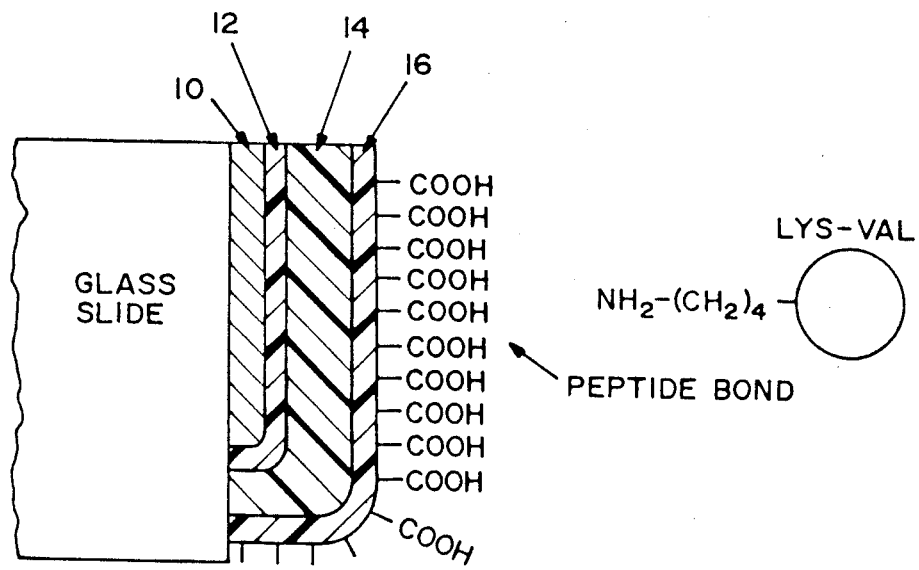
FIG. 2 is a cross-sectional view of fabricated membrane layers deposited on a hybrid gate for use in a conventional MOSFET.

Alternative embodiments of the present invention include employing multi-layer derivatized membranes connected to the gate of a MOSFET to function as a hybrid ion-sensitive gate (FIG. 2). For example, several combinations of monomers and of carrier gases may be used to develop adhesive (12), insulating (14), and reactive (16) layers. As illustrated in FIG. 2, an initial layer is constructed using 10% nitrogen in the presence of an adhesion promoting monomer, such as PFDMC or styrene. This layer may be employed as an interfacial material between the metal electrode (10) and other membrane layers. The adhesive layer (12) may be in the range of 200–800 A, preferably 200–300 A. Next, an insulating layer (14) is deposited as a middle layer using a monomer optimized for dielectric strength, such as, for example, PFDMC, paralene or silicon in the presence of nitrogen or argon to develop an approximately 1,000–10,000 A high capacitance middle layer, preferably 5000 A.

As an outer layer, a functionalized layer (16) having carboxyl groups to which lysine-modified valinomycin can be covalently bound is constructed. The outer layer being approximately 200–1,000 A, preferably 200–300 A in depth, can be developed using PFDMC or acetylene in the presence of oxygen.

This multi-layer membrane can then be covalently bound through the reactive amine of the lysine-valinomycin molecule with carboxyl groups present on the functionalized outer layer and subsequently connected to a solid-state sensor.

C. Coupling of Valinomycin

The active site-containing polymer in either its permeable conductive form or insulating form is covalently coupled to the lysine-modified valinomycin. In some cases this is done directly; in other cases an intervening spacer is inserted. These spacers can be from about 1 to about 20 and especially from about 1 to about 12 atoms long. They are organic groups which are bifunctional so as to be able to covalently bond to the polymer and to the modified lysine. They can be inherently heterobifunctional or they can be homobifunctional in which case they are used in combination with a second agent to effect one of the two couplings in a selective fashion. These spacer arms can be selected from the large family of materials provided in the art for immobilizing active groups onto substrates and are reviewed in Akela, A., and Sherrington, D. C., *Chem Rev* 81:557–587 (1981). Typical heterobifunctional agents include 1-amino, n-hydroxy, n-alkanes, 1- amino-n-hydroxy-n-alkanes, succinimidyl 4-(p-maleimidophenyl)butyrate and cyanuric chloride. Typical homobifunctional spacers include the 1,n-diamino-n-alkanes, which are commonly used in combination with an active anhydride or diacid or other amine to amine coupling agents such as the carbodiimides or the like to complete the coupling; other homobifunctional coupling agents include imidoesters, such as dimethyl adipimidate (DMA), dimethyl pimelimidate (DMP) and dimethyl suberumidate (DMS); N-hydroxysuccinimide esters, such as disuccinimidyl suberate; difluorodinitrobenzene; and 4,4′-diisothiocyano-2,2′-disulfonic acid stilbene.

The spacer can be coupled to the lysine-modified valinomycin and then coupled to the polymer or the spacer can be coupled to the polymer and this combination coupled to the lysine-modified valinomycin. The first route is shown in a typical process which involves the treatment of surface acid groups on the polymer with thionyl chloride (see Snell and Keenan, *Chem Soc Rev* 8(2):259–282 (1979) to form the reactive acid chloride. Coupling of species with pendant amino groups, such as lys-val or an amino-terminated spacer-linked lys-val, is then accomplished via reaction of the primary (terminal) amine with the acid chloride sites to form an amide-bonded product. This is shown in the generic reaction sequence involving a typical amine-terminated spacer-coupled lysine-modified valinomycin, shown as $H_2N(CH_2)_x..R$, as follows:

$$M-COOH \xrightarrow{SOCl_2} M-COCl \xrightarrow{H_2N(CH_2)_x..R} M-CONH(CH2)_x..R + HCl$$

where M=membrane surface; x is an integer from say 1 to 12; R=lys-val. As one skilled in the art would appreciate, because HCl is a product of the amide reaction, a hindered organic base such as N,N-dimethylbenzylamine may be added so that protonation of the amine precursor does not occur and the desired coupling is achieved.

Another procedure useful in the practice of the invention for attaching amines to carboxylic acids involves the use of diimide coupling reagents (Kunz, H. *Angew Chem Int Ed Engl* 17(1):67–68 (1978) and Lenhard and Murray, *J Amer Chem Soc* 100(25):7870–7875 (1981)) to perform a single-step coupling as illustrated below. This is a preferred method as it allows for minimization of unwanted side reactions and provides flexibility of solvent choice for the reaction, such as aqueous buffers:

$$M-COOH + NH_2R \xrightarrow{R'N=C=NR'} M-CONHR + R'NHCONHR', \text{ wherein}$$

R is the lys-val residue and each of the two R′ groups are organic groups such as alkyls, cycloalkyls and the like.

The second preparation scheme wherein the spacer is coupled to the backbone first and then the valinomycin is attached is exemplified as follows: In this embodiment, the length of the spacer holding the valinomycin molecule to the membrane surface is varied by the following multi-step scheme, illustrated below, similar to procedures used in solid-phase peptide synthesis. In the basic example given, 1,n-diamino-n-alkane linkages are first attached to the active attachment sites on the membrane using an appropriate coupling agent such as an acid halide or a carbodiimide or the like as needed. This reaction is then followed by coupling of the primary amine of the lysine-modified valinomycin to the terminal amine provided by the spacer, using suitable amine-to-amine coupling reagents such as glutaraldehyde, maleic anhydride or succinic anhydride. This coupling is shown by the following generic formula:

$$M-COOH + H_2N-(CH_2)_2-NH_2 \xrightarrow{DCC} M-CONH(CH_2)_nNH_2 \xrightarrow[NH_2R']{SA} M-CONH(CH_2)_2NHCO(CH_2)_2CONHR'$$

where n is an integer from 1 to 12; $NH_2R'$=lys-val; SA=succinic anhydride; and M-COOH is a carboxylated membrane surface.

These various coupling techniques can find application with both the permeable conductive membrane materials and the relatively impermeable insulative materials.

Success of the various coupling reactions may be determined by chemical analysis of the polymeric products (elemental analysis, NMR spectroscopy, among other methods). The surface binding capacity (ions/$cm^2$) of membranes modified with immobilized valinomycin may be determined by complexation of the radionuclide $^{86}Rb^+$by the valinomycin receptor. Experiments involving the determination of binding and selectivity of lysine-modified-valinomycin using $^{86}Rb^+/K^+$mixtures have demonstrated the efficacy of the radiolabel technique. For a 1 $cm^2$ modified membrane, and valinomycin coverage of $10^{-11}$ mole/$cm^2$, a signal of greater than 1500 cpm is expected for 100% $^{86}Rb^+$complexation.

Solid State Device Design

A major use for the insulative membranes having covalently bonded valinomycin is to incorporate them into solid-state sensors so as to impart potassium ion selectivity to the sensors. In one such device, the insulative membranes can be laid down directly upon the gate region of a field effect transistor (FET). Another typical application of an insulating membrane in a solid state device can follow the design by Afromowitz and Yee (*J*

Bioeng 1:55-60 (1977)). In this design, planar gold film electrodes coated with the insulative derivatized membranes of the present invention are electrically connected to a metal oxide gate of a conventional MOSFET. The MOSFET device is then operated in the constant-drain-current mode using a calomel reference electrode.

At a constant drain current, a change in activity of target ions in solution, leading to a change in the potential at the membrane/solution interface, is directly reflected as the change in the gate voltage measured with respect to the reference electrode:

$$V_G = V_{FB} - \frac{Q_S}{C_G} + O_S$$

where $V_G$=gate voltage, $V_{FB}$=flat band potential, $Q_s$=charge density in the surface inversion layer and space charge region, $C_G$=capacitance of gate insulator, and $O_s$=surface potential of semiconductor.

As can be seen, the ion-selective gate embodied in the present invention may be manufactured separately from an FET, and then connected to a conventional metal oxide gate on an FET to make a hybrid potassium-sensitive FET or sensor. This design allows the ion-sensitive portion of the gate to be isolated from the electronics. The hybrid gate can be fabricated independently and later immersed in solution for testing and use without worry about encapsulation problems, which have until now been a major technological barrier to biosensor and ion sensor use.

EXAMPLES

Synthesis of Lysine-Valinomycin

The derivatized analog of valinomycin, lysine-valinomycin (lys-val) was built upon a polystyrene support by stepwise segment condensation and cyclization, as described by Gisin and Dhundale, 1969, supra. The segments used were t-butyloxyisovaleric acid and t-butyloxycarbonyl-$N_E$-p-nitrobenzyloxycarbonyl-L-lysyl-D-(alpha)hydroxyisovaleric acid and they were prepared by demonstrated methods taught by Gisin et al, 1979, supra and Losse and Bachman, Chem Ber 97:2671 (1964). Purity of the product was verified by thin-layer chromatography, amino acid analysis, and mass spectroscopy.

The ability of the lys-val to bind $K^+$ was assessed using $^{86}Rb^+$. In a two-phase mixture, valinomycin migrates to the organic phase while free $Rb^+$ stays in the aqueous phase. Only $Rb^+$ that has bound to the valinomycin is carried to the organic phase. Results indicated that for $Rb^+$ concentrations greater than 0.9 mM, the lys-val was nearly as competent as native valinomycin in binding $Rb^+$. For [$Rb^+$] between 0.1 and 0.3 mM, lys-val appeared be approximately 50% less efficient than native valinomycin.

Immobilization of Lys-Val on PVC-COOH and Formation of Permeable Membranes

To test the feasibility of using carboxyl-substituted PVC as a substrate for a conducting membrane with immobilized components, several experiments using conventional ISEs were conducted as follows.

Potentiometric measurements were made using an ORION 501 pH/ISE meter with an ORION 90-02 double junction reference electrode (Ag/AgCl; outer solution, 1 M $NH_4NO_3$). The experimental membranes were tested using a Philips Model IS-561 electrode body. Four membrane types were tested; lys-val immobilized on a PVC-COOH polymer with dioctylsebacate (DOS) plasticizer, unbound lys-val in PVS/DOS membrane, valinomycin in PVC/DOS membrane, and a blank (no carrier) PVC-COOH/DOS membrane.

To immobilize lys-val on carboxylated PVC substrate, a solution of 100 mg carboxylic-acid-substituted PVC (PVC-COOH, 1.7% COOH, Aldrich) in 6 ml THF was treated at $-20°$ C. with 0.825 mg (4 umole) N,N'-dicyclohexylcarbodiimide (Aldrich), 0.675 mg (5 umole) 1-hydroxybenzotriazole hydrate (Aldrich), and 3.0 mg (2.6 umole) lys-val. The solution was stirred for 2 hours at $-20°$ C. and for 12 hours at room temperature. Solvent was removed under vacuum and the residue triturated with 20 ml 95% ethanol in an ultrasonic bath. The polymer suspension was filtered, washed with ethanol, and air-dried (yield 75 mg).

To prepare lys-val/PVC-COOH permeable membranes and electrodes, the immobilized valinomycin/PVC-COOH product (33.9 mg) was dissolved in 2 ml THF along with 65 mg DOS, cast in a 14-mm-diameter glass ring on a glass plate, and the solvent allowed to evaporate at $45°$ C. ISEs were prepared from discs 4 mm in diameter and 0.1 to 0.2 mm thick, cut from the membrane, and inserted into a Model IS-561 Philips liquid membrane electrode body. The internal filling solution was $10^{-2}$ mole KCl and the internal reference electrode was Ag/AgCl.

Figure 3:
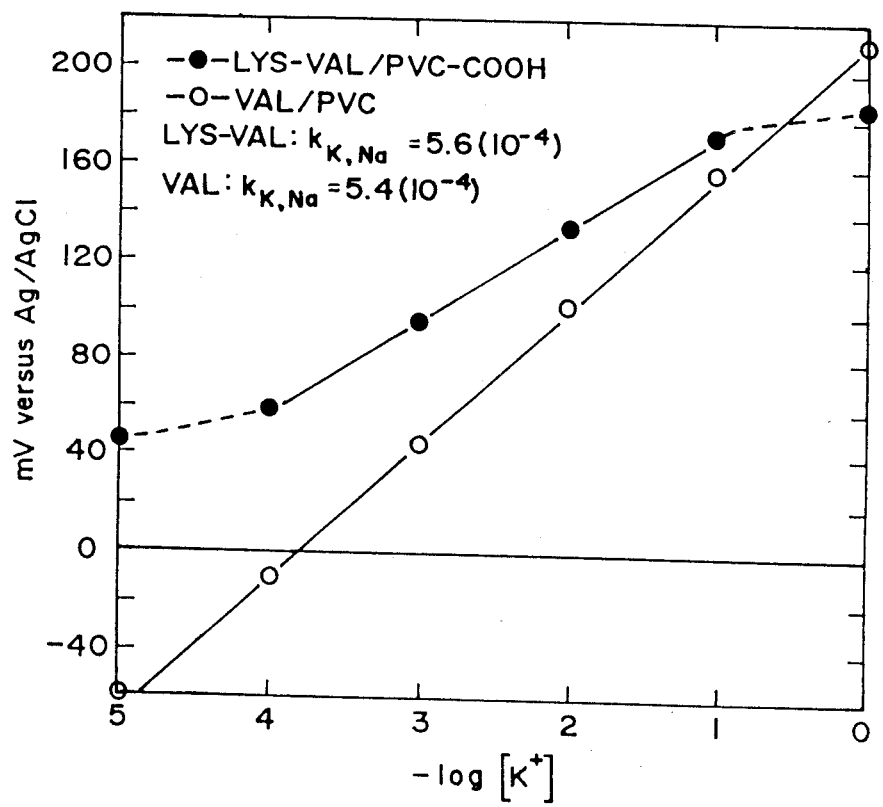
FIG. 3 is a graph which illustrates the response of immobilized lysine-modified valinomycin and free valinomycin electrodes to KCl in the presence of 0.1 M NaCl.

The potentiometric response of valinomycin and membrane-bound lys-val based electrodes to [$K^+$] ranging from $10^{-5}$ to 1 M, in the presence of 0.1 M NaCl, is shown in FIG. 3. A linear response over four decades, with Nernstian slope (56.5 mV) was obtained for valinomycin. Immobilized lys-val membrane electrodes exhibited a linear response over three decades with a sub-Nernstian slope of 38.3 mV. Selectivity coefficients, $k_{K,Na}$, were $5.4 \times 10^{-4}$ and $5.6 \times 10^{-4}$ for valinomycin and bound lys-val, respectively.

Electrodes prepared from immobilized lys-val/PVC-COOH membranes required lengthy periods of soaking in 0.01 M KCl prior to acceptable stable response, typically greater than 5 days, such as 5 to 30 days. Decreased mobility of the receptor ligand in the polymer matrix may result in an induction period during which ion-conductive "channels" ($K^+$/valinomycin complexes) are gradually established. Varying the concentration of lys-val and length of spacer is expected to alter the soaking period. Membrane resistances also remain high during the several days prior to acceptable [$K^+$] response. Unbound lys-val membrane electrodes did not yield stable signals in $K^+$ solutions even after prolonged soaking. Leaching of the water-soluble unbound lys-val from the membrane was observed.

Preparation of Plasma-deposited Insulative Polymers

The plasma-polymerized films are deposited in a laboratory vacuum system (P. Datta et al, "The Properties of Fluorocarbon Films Prepared by Plasma Polymerization of 1,3-perfluorodimethylcyclohexane," 4th Instrumentation Symposium on Plasma Chemistry, Sept. 1979; and Kaganowicz and Robinson, J Vac Sci Technol A4(4):1901-1904). This system employs a small (20"×30") magnetron plasma-discharge reactor utilizing a continuous flow of the reacting gasses and parallel screen electrodes with 30% open structures to confine the primary glow to a "race track" on the screen surface. The gases to be reacted in the glow discharge are introduced at the top of the bell jar, to prevent gas-phase polymerization in the vicinity of the electrodes. The precursors and carrier gases are mixed before introduction.

Typically, the process begins using pure carrier gas (Ar, Ne) because this has a cleaning action, similar to sputtering a surface, and results in better adhesion. The monomer is then introduced and the gas mixture is controlled to provide the mixture and profile desired. The interfaces between layers of different compositions change gradually over a distance on the order of ~100 Å and eliminate sharp discontinuities. The rate of the gas flow into the system is maintained at a specified value using flowmeters. Pressure is maintained constant for each experiment by adjusting the pumping speed to maintain a specified pressure for a given flow of gas. The pressure in the system is measured using an MKS Baraton capacitive probe, which is not sensitive to the composition of the gas mixtures. The relative positions of the gas sources and sinks with respect to the probe and to the discharge areas are maintained constant throughout the deposition experiments as their relative position is critical for maintaining deposition rate and film composition. The substrate is rotated between the electrodes so that the areas of interest are exposed uniformly to the vertical bars of the race track to achieve uniform deposit. A 13.5 kHz power supply provides a power density in the race track region of 0.3–2.5 W/cm$^2$. The substrate to be coated is placed on a grounded plate and the potential between the electrodes maintained at about 1,000 V. The power levels during the plasma depositions are varied to control cross-linking density of the glow-deposited film.

In accordance with the above discussion, membranes of PFDMC were conventionally plasma-deposited in the presence of added N$_2$ over gold electrodes. Glow-discharge or plasma-deposited polymers have been studied primarily in vacuum and in air. Since the plasma-deposited membranes are used in a saline environment, experiments were conducted to evaluate properties of glow-discharge polymers in an aqueous environment. The dc capacitance was measured for 5000-Angstrom films to be 100 pF in normal atmosphere and 50 pF in either distilled water or 0.17 NaCl. The capacitance was stable over 4 hours in aqueous solution.

Infrared transmittance spectrum of the glow-discharge polymer was measured as well. This was carried out by depositing a polymer using the above-noted method on a silicon substrate. The glow-discharge polymer made from a monomer mixture of 1,3,-PFDMC and nitrogen. The transmittance spectrum showed a band at 1220 cm$^{-1}$ characteristics of a carbon-fluorine vibrational mode and one at 1760–70 cm$^{-1}$. The bands in the region 1100–450 cm$^{-1}$ were due to the silicon substrate. The band near 3300 cm$^{-1}$ may be a hydroxyl mode representing the instrument background; the band does not appear in the polarized reflection spectra. The transmittance spectrum was obtained using the microscope attachment on a Digilab FTS-60 FTIR spectrometer.

The permeability of the glow-discharge polymers was also tested. Aluminized metal mirrors were coated with the same monomer mixture as above, and then submerged in either deionized water or water containing 0.17 M NaCl at 80° C. for ½ hour. (Physiologic saline is 0.14 M NaCl.) Polarized reflectance spectra were recorded after the plasma-deposited film on aluminum was: (a) exposed to hot water for one-half hour and (b) exposed to a hot solution of NaCl (10 mg/ml). No change in the spectral features of the film was observed after these treatments. Chloride is a catalyst for the hydrolysis of aluminum metal and is the cause of most corrosion in aluminum thin films, e.g., in plastic-encapsulated IC devices. The absence of aluminum corrosion in the NaCl solution indicates that chloride does not migrate readily through the insulative fluoropolymer film.

The polymer film was treated with oxygen plasma to introduce surface carboxyl groups. The film surface was then treated for 2 hours at 5° C. with a solution of dicyclohexylcarbodiimide and N-hydroxysuccinimide in THF to activate the carboxylic acid groups. After rinsing with water, the film surface was then treated with a solution of lys-val in pH 10 acetate buffer for 12 hours at room temperature, resulting in formation of an amide bond between the free lysine NH$_2$ of the lys-val and the surface carboxylic acid groups.

The invention has been described in detail with particular reference to preferred embodiments thereof, but it will be understood that variations and modifications can be effected within the spirit and scope of the invention.

We claim:

1. A stabilized potassium ion-selective membrane comprising lysine-substituted valinomycin covalently bonded to an active site-containing hydrophobic polymer substrate.

2. The membrane of claim 1 wherein the active site is selected from the group consisting of carboxylic acid, carbonyl, hydroxyl, and amide groups.

3. The membrane of claim 2 wherein the hydrophobic polymer substrate is fabricated to form a plasticized, high impedance, conducting membrane.

4. The membrane of claim 3 wherein the hydrophobic polymer comprises polyvinyl chloride.

5. The membrane of claim 2 wherein the membrane is liquid impermeable.

6. The membrane of claim 1 wherein the valinomycin is covalently bonded to the polymer substrate through an amide bond formed from the amine of the lysine substituent and a carboxylic acid group of the substrate.

7. The membrane of claim 1 wherein a spacer arm is inserted between the reactive amine of the lysine residue and the substrate.

8. The membrane of claim 7 wherein the spacer arm is an organic spacer arm from about 1 to about 20 atoms in length.

9. The membrane of claim 7 wherein the spacer arm is covalently bonded at one end to the primary amine of the lysine residue and at the other end to a carboxylic acid group of a carboxylated polymer.

10. The membrane of claim 9 wherein the reactive spacer arm comprises a linear diaminoalkane of the formula NH$_2$(CH$_2$)$_n$NH$_2$, wherein n is an integer from 1 to 10.

11. The membrane of claim 1 wherein the membrane is insulating.

12. In a potassium ion selective sensor wherein potassium ion selectivity is imparted by the selective association of potassium ion with a valinomycin species, the improvement comprising employing as the valinomycin species, a lysine substituted valinomycin covalently bonded via the amine group of the lysine to a polymer.

13. The sensor of claim 12 wherein the polymerbound valinomycin is in the form of a liquid permeable membrane.

14. The sensor of claim 13 configured as a potassium ion-selective electrode comprising:
   an internal reference element having a predetermined concentration of salt solution; and
   in physical contact with said reference element, a hydrophobic potassium ion-selective membrane comprising a lysine derivative of valinomycin covalently bonded through the amine group of the lysine to an active site on the polymer.

15. The sensor of claim 12 wherein the polymer bound valinomycin is in the form of a liquid impermeable membrane.

16. The sensor of claim 15 wherein the membrane is insulating.

17. The sensor of claim 15 configured as a solid state semiconductor device.

18. The sensor of claim 17 wherein the solid state semiconductor device is a field effect transistor with said liquid impermeable membrane being an insulating membrane over its gate region.

19. The sensor of claim 18 further comprising at least one silicon layer adjacent to said insulating membrane.

20. The sensor of claim 17 wherein the membrane is formed using glow discharge polymerization of an organic monomer with a carrier gas.

21. The sensor of claim 20 wherein the organic monomer is selected from the group consisting of 1,3-perfluorodimethylcyclohexane, acetylene, paralene and styrene.

22. The sensor of claim 20 wherein the carrier gas comprises a member selected from the group consisting of nitrogen, oxygen and argon.

* * * * *